(12) United States Patent
Bergelson et al.

(10) Patent No.: US 7,299,085 B2
(45) Date of Patent: Nov. 20, 2007

(54) REMOTE MONITORING OF IMPLANTED MEDICAL DEVICE AND SURFACE ECG SIGNALS

(75) Inventors: Michael Bergelson, Bronx, NY (US); Narcis M. Naydenov, Wayne, NJ (US)

(73) Assignee: Medtronic, Inc., Minneapolis, MN (US)

( * ) Notice: Subject to any disclaimer, the term of this patent is extended or adjusted under 35 U.S.C. 154(b) by 478 days.

(21) Appl. No.: 10/422,533

(22) Filed: Apr. 23, 2003

(65) Prior Publication Data

US 2004/0215089 A1 Oct. 28, 2004

(51) Int. Cl.
*A61B 5/04* (2006.01)
*A61B 5/0402* (2006.01)

(52) U.S. Cl. .................. 600/509; 128/903; 128/904

(58) Field of Classification Search .............. 600/509, 600/522, 523; 128/903, 904; 607/30, 32, 607/60, 27
See application file for complete search history.

(56) References Cited

U.S. PATENT DOCUMENTS

| | | | | |
|---|---|---|---|---|
| 4,337,377 A | * | 6/1982 | Van Riper et al. | 379/106.02 |
| 4,374,382 A | * | 2/1983 | Markowitz | 340/870.01 |
| 4,791,936 A | | 12/1988 | Snell et al. | 128/697 |
| 5,289,824 A | * | 3/1994 | Mills et al. | 600/508 |
| 5,467,773 A | * | 11/1995 | Bergelson et al. | 600/522 |
| 5,669,391 A | | 9/1997 | Williams | 128/697 |
| 5,987,352 A | | 11/1999 | Klein et al. | 600/509 |
| 6,412,490 B1 | | 7/2002 | Lee | 128/897 |
| 6,485,416 B1 | * | 11/2002 | Platt et al. | 600/300 |
| 2002/0082665 A1 | * | 6/2002 | Haller et al. | 607/60 |
| 2002/0193846 A1 | | 12/2002 | Pool et al. | |
| 2003/0114896 A1 | | 6/2003 | Boute et al. | |

FOREIGN PATENT DOCUMENTS

| | | |
|---|---|---|
| EP | 0 472 411 A1 | 8/1991 |
| WO | WO 99/45516 | 9/1999 |
| WO | WO 01/13791 | 3/2001 |
| WO | WO 01/70101 | 9/2001 |
| WO | WO 02/34332 A1 | 5/2002 |

* cited by examiner

*Primary Examiner*—Carl Layno
*Assistant Examiner*—Yun Haeng Lee
(74) *Attorney, Agent, or Firm*—Daniel G. Chapik (57) ABSTRACT

An integrated device for remote monitoring of implanted medical devices and surface ECG information includes components for collection of information from an implanted medical device, collection of surface ECG information, and remote communication of the collected information to a remote monitoring station. The remote monitoring station controls operation of the integrated device to automatically acquire the information without substantial patient intervention. In this manner, the device promotes accurate and timely collection of the information, and reduced depletion of battery resources within the implanted medical device.

59 Claims, 12 Drawing Sheets

REMOTE MONITORING OF IMPLANTED MEDICAL DEVICE AND SURFACE ECG SIGNALS

TECHNICAL FIELD

The invention relates to remote monitoring of medical patients and implanted medical devices.

BACKGROUND

Implanted medical devices, such as pacemakers, typically include wireless telemetry circuitry to permit monitoring and programming of the device by an external monitor or programmer. In addition, some monitors and programmers include a telecommunication interface to communicate remotely with a remote monitoring station. In this manner, some monitors and programmers support remote monitoring and programming of implanted medical devices, e.g., via a dial-up telephone connection or network connection.

Typically, to commence monitoring, a remote monitoring station operator calls a patient and establishes a two-way telephone connection. A person at the remote monitoring station guides the patient to set up the connection, place surface electrodes on the patient's chest for surface ECG recording, and turn on the monitor or programmer to interrogate the pacemaker implanted within the patient. In particular, the patient places a wand that contains a radio frequency (RF) antenna in proximity with the implanted pacemaker.

The monitor or programmer receives data from the implanted pacemaker and stores the data for communication to the remote monitoring station, e.g., via a telephone or network connection. In addition, data collected from the surface ECG recording is transmitted to the remote monitoring station, typically using transtelephonic frequency modulation (FM). Collection and transmission of implanted medical device data and surface ECG data in this manner is useful in providing the remote monitoring station with remote access to critical patient information.

Existing systems place great reliance, however, on the patient to take certain actions in a timely and accurate manner. To ensure accurate data recording, for example, the patient must be trained to quickly and accurately position the wand and ECG monitoring electrodes. If the patient is not sufficiently adept in handling wand or electrode placement, interrogation may take longer than desired, possibly resulting in undue depletion of the pacemaker battery.

Thus, inappropriate actions on the part of the patient can be a significant problem in affecting longevity of a pacemaker. With implantable cardioverter/defibrillators (ICD), it is even more important to interrogate the device as well as assess surface ECG simultaneously. Collecting the surface ECG recording in combination with retrieving the contents of the implanted medical device can yield additional clinical information in the assessment of the operation of the implanted medical device.

SUMMARY

In general, the invention is directed to an integrated device for remote monitoring of implanted medical devices and surface ECG information. The integrated device includes components for collection of information from an implanted medical device, collection of surface ECG information, and remote communication of the collected information to a remote monitoring station. In some embodiments, the remote monitoring station controls operation of the integrated device to automatically acquire the information without substantial patient intervention. In this manner, the device promotes accurate and timely collection of the information, and reduced depletion of battery resources within the implanted medical device.

In one embodiment, the invention provides a patient monitoring device comprising a telemetry interface to collect device information from an implanted medical device within a patient, a surface electrocardiogram (ECG) interface to collect surface ECG information from the patient, a telecommunication interface to transmit the device information and the surface ECG information to a remote monitoring station.

In another embodiment, the invention provides a method comprising collecting device information from an implanted medical device within a patient, collecting surface electrocardiogram (ECG) information from the patient, and transmitting the device information and the surface ECG information to a remote monitoring station via a common telephone interface.

In an added embodiment, the invention provides a patient monitoring system comprising a remote monitoring station, and a patient monitoring device including a telemetry interface to collect device information from an implanted medical device within a patient, a surface electrocardiogram (ECG) interface to collect surface ECG information from the patient, a telecommunication interface to transmit the device information and the surface ECG information to the remote monitoring station.

The details of one or more embodiments of the invention are set forth in the accompanying drawings and the description below. Other features and inventive aspects of the invention will be apparent from the description and drawings, and from the claims.

DETAILED DESCRIPTION

Figure 1:
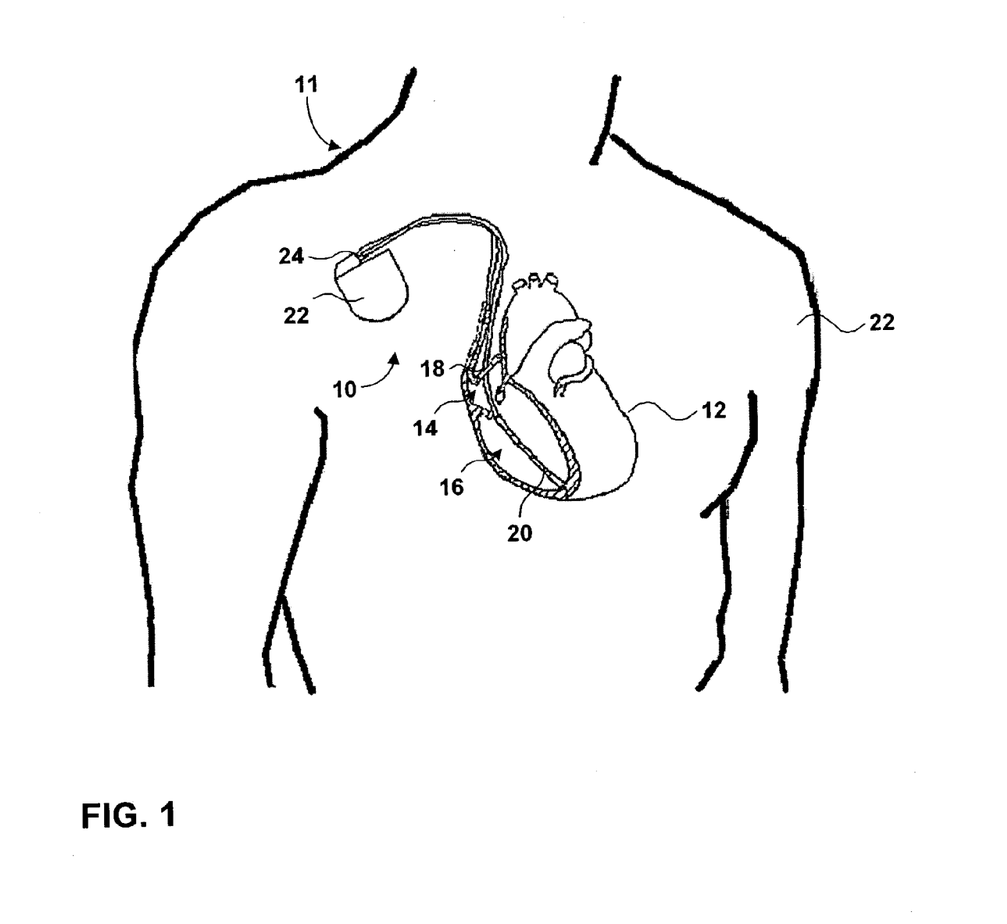
FIG. 1 is a schematic illustration of an implantable medical device with leads extending to a human heart.

FIG. 1 depicts an exemplary implantable medical device (IMD) 10 with a patient 11. In accordance with the invention, an integrated patient monitoring device is designed to collect device information from IMD 10 via radio frequency (RF) telemetry, and surface ECG information from patient 11 via surface electrodes. As will be described, the integrated patient monitoring device includes a telecommunication interface for remote transmission of the collected information to a remote monitoring station. In some embodiments, the remote monitoring station controls operation of the integrated device to automatically acquire the information without substantial patient intervention.

IMD 10 delivers pacing pulses or other stimulation therapy to heart 12. In the example of FIG. 1, IMD 10 is an implantable, multi-chamber pacemaker that includes cardioversion and defibrillation capabilities. The invention is not limited to the particular IMD and configuration shown in FIG. 1, however, but may be practiced with a variety of implantable medical devices. The invention may be practiced, for example, with IMDs that pace a single cardiac chamber or several chambers, including one or more atria or one or more ventricles, as well as IMDs that lack cardioversion and defibrillation capability.

IMD 10 includes an implantable pulse generator (IPG) to generate pacing stimuli to administer one or more therapies to heart 12. In the embodiment shown in FIG. 1, pacing stimuli are applied to the right atrium 14 or the right ventricle 16, or both. IMD 10 also includes circuitry to sense atrial and ventricular activations. Atrial and ventricular bipolar pace/sense electrode pairs at the distal ends of leads 18 and 20, respectively, carry out the pacing and sensing functions. IMD 10 includes a housing 52 that may serve as a "can" electrode. A connector block 24 receives proximal ends of leads 18, 20.

In operation, IMD 10 senses and records EGM information obtained via electrodes carried by leads 18, 20 and, optionally, the can electrode provided by housing 22. IMD 10 stores the EGM information and IMD parameters in a memory associated with the IMD. IMD 10 also stores program instructions for delivery different pacing therapies to heart 11. In addition, IMD 10 includes an RF telemetry interface that permits programming of the IMD and interrogation of the IMD to collect device information including the EGM information or IMD parameters. The EGM information may be associated with particular episodes recorded by IMD 10.

Figure 2:
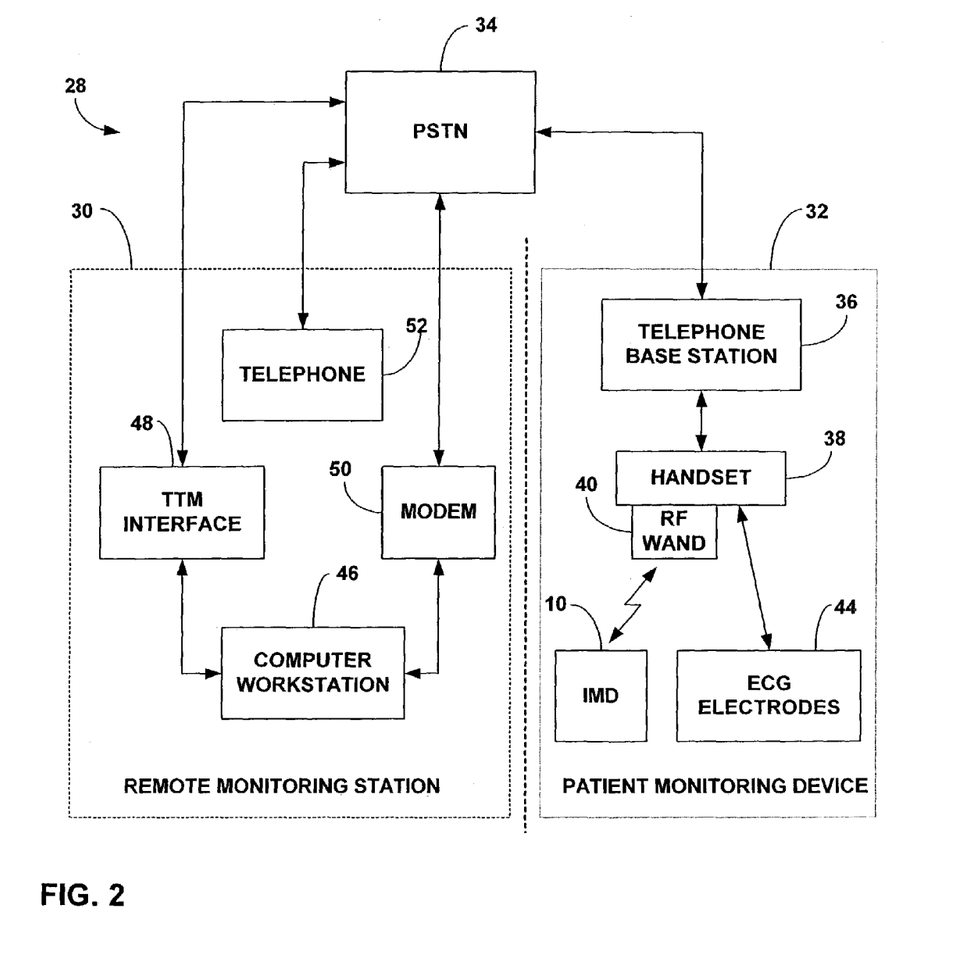
FIG. 2 is a block diagram illustrating a system for remote communication with a patient and an implanted medical device within the patient.

FIG. 2 is a block diagram illustrating a system 28 for remote communication with patient 11 and IMD 10 within the patient. As shown in FIG. 2, system 28 includes a remote monitoring station 30 and a patient monitoring device 32. Patient monitoring device 32 integrates features for collection of device information from IMD 10 and collection of surface ECG information from patient 11. In this manner, patient monitoring device 32 performs dual functions in a single device, providing the operator with convenience and simplicity. In addition, in some embodiments, patient monitoring device 32 is responsive to control signals transmitted by remote monitoring system 30.

As shown in FIG. 2, remote monitoring station 30 and patient monitoring device 32 communicate with one another via public switched telephone network (PSTN) 34. Patient monitoring device 32 includes a telephone base station 36 including a telecommunication interface for communication with PSTN 34. In the example of FIG. 2, patient monitoring device 32 includes a telephone handset 38 coupled to telephone base station 36, e.g., via a wired connection 37 or wireless connection.

Handset 38 includes an integrated RF telemetry wand 40 for communication with IMD 10 to collect device information including EGM information and device parameters. In addition, handset includes a surface ECG interface to collect surface ECG information from ECG electrodes 44. ECG electrodes 44 are placed in contact with patient 11 to collect ECG information.

Handset 38 communicates the collected information to telephone base station 36, which then relays the information to remote monitoring station 30 via PSTN 34. As will be described, telephone base station 36 transmits the surface ECG information using transtelephonic frequency modulation (FM) in real time. Telephone base station 36 transmits the device information using a data modem. The device information and surface ECG information can be communicated during the course of a single telephone call.

Remote monitoring station 30, in the example of FIG. 2, includes a computer workstation 46 coupled to a transtelephonic interface 48 and a modem 50. Remote monitoring station 30 also includes a telephone 52. A remote monitoring station operator uses telephone 52 to communicate with patient 11. For example, the operator initiates a telephone call to patient 11 to guide the patient through set-up procedures to establish a call for transfer of collected device information and surface ECG information.

Transtelephonic interface 48 receives and demodulates the surface ECG information transmitted by patient monitoring device 32. Modem 50 receives and demodulates the device information transmitted by patient monitoring device 32. Computer workstation 46 processes the demodulated surface ECG information and device information to archive and display the information for review by an operator associated with remote monitoring station 30. For example, computer workstation 46 may generate a patient database record containing the device information and the surface ECG information.

Remote monitoring station 30 and patient monitoring device 32, in some embodiments, coordinate transmission of device information and surface ECG information. For example, patient monitoring device 32 is responsive to control signals transmitted by remote monitoring station 30 to transmit surface ECG information in real time via transtelephonic modulation. When a sufficient amount of surface ECG information has been collected, patient monitoring device 30 transmits buffered device information to remote monitoring station 30.

In some embodiments, patient monitoring device 32 includes time markers in the surface ECG information transmitted to remote monitoring station 30. Patient monitoring device 32 generates the time markers every few seconds to indicate that, during transmission of the surface ECG information in real time, the device information continues to be collected and buffered. In this manner, an operator associated with remote monitoring station 30 can view the real time surface ECG information and verify, by observing the time markers, that patient monitoring device 32 is collecting the device information.

If the time markers are not present in the real-time surface ECG information, the operator determines that patient monitoring device 32 is not collecting device information. In this case, the operator may instruct patient 11, via the telephone interface, to more accurately position handset 38 and wand 40 relative to IMD 10. Consequently, the operator can verify accurate and timely collection of the device information, and thereby avoid undesirable depletion of battery resources within the implanted medical device. In particular, the operator can reduce the number of ineffective data collection attempts, and hence the number of power-draining telemetry sessions initiated with IMD 10.

Figure 3:
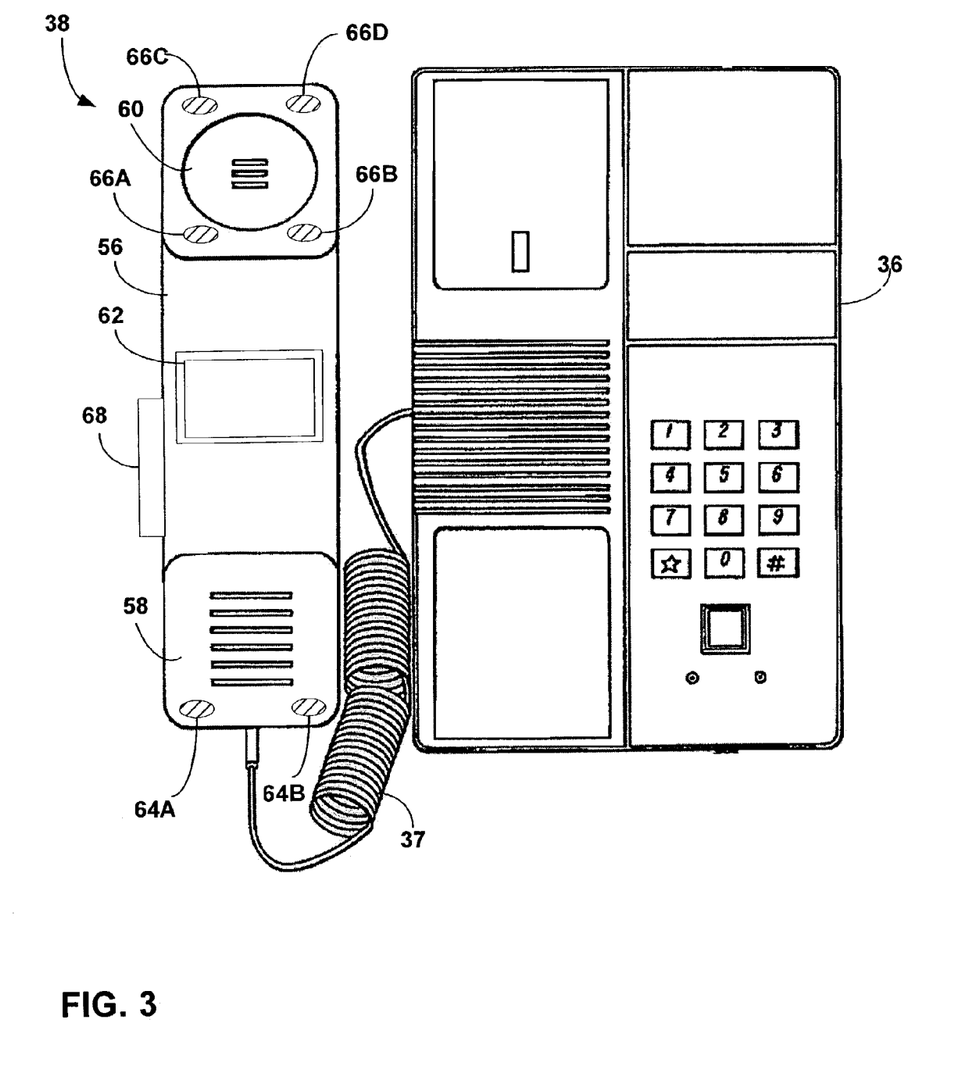
FIG. 3 is a diagram of a telephone handset forming part of a device for remote monitoring of implanted medical devices and surface ECG information.

FIG. 3 is a diagram of a telephone handset 38 forming part of a patient monitoring device 32. As shown in FIG. 3, handset 38 includes a housing 56, a microphone 58, a speaker 60, and an RF telemetry wand 62. Microphone 58 and speaker 60 may be entirely conventional telephone components capable of transmitting and receiving voice information. RF telemetry wand 62 is designed to communicate with IMD 10 when placed in proximity with the IMD. Accordingly, handset 38 or telephone base station 36 includes appropriate telemetry interface circuitry to drive RF telemetry wand 62 for communication with IMD 10. As an alternative, handset 38 may be entirely self-contained in the form of a mobile telephone such as a cellular phone, personal digital assistant, or other devices with wireless telecommunication capabilities.

Handset 38 also includes a first set of surface ECG electrodes 64A, 64B (collectively electrodes 64) and a second set of electrodes 66A, 66B, 66C, 66D (collectively electrodes 66). Handset 38 obtains surface ECG information sensed across electrodes 64, 66. Electrodes 64 may be coupled to one another. Similarly, electrodes 66 may be coupled to one another. In this manner, electrodes 64 and 66 present multiple electrode surfaces for contact with the chest of patient 11. As an alternative to electrodes 64, 66, handset 38 includes a port 68 to receive an electrode cable coupled to external, adhesive- or gel-backed surface electrodes (not shown in FIG. 3).

Figure 4:
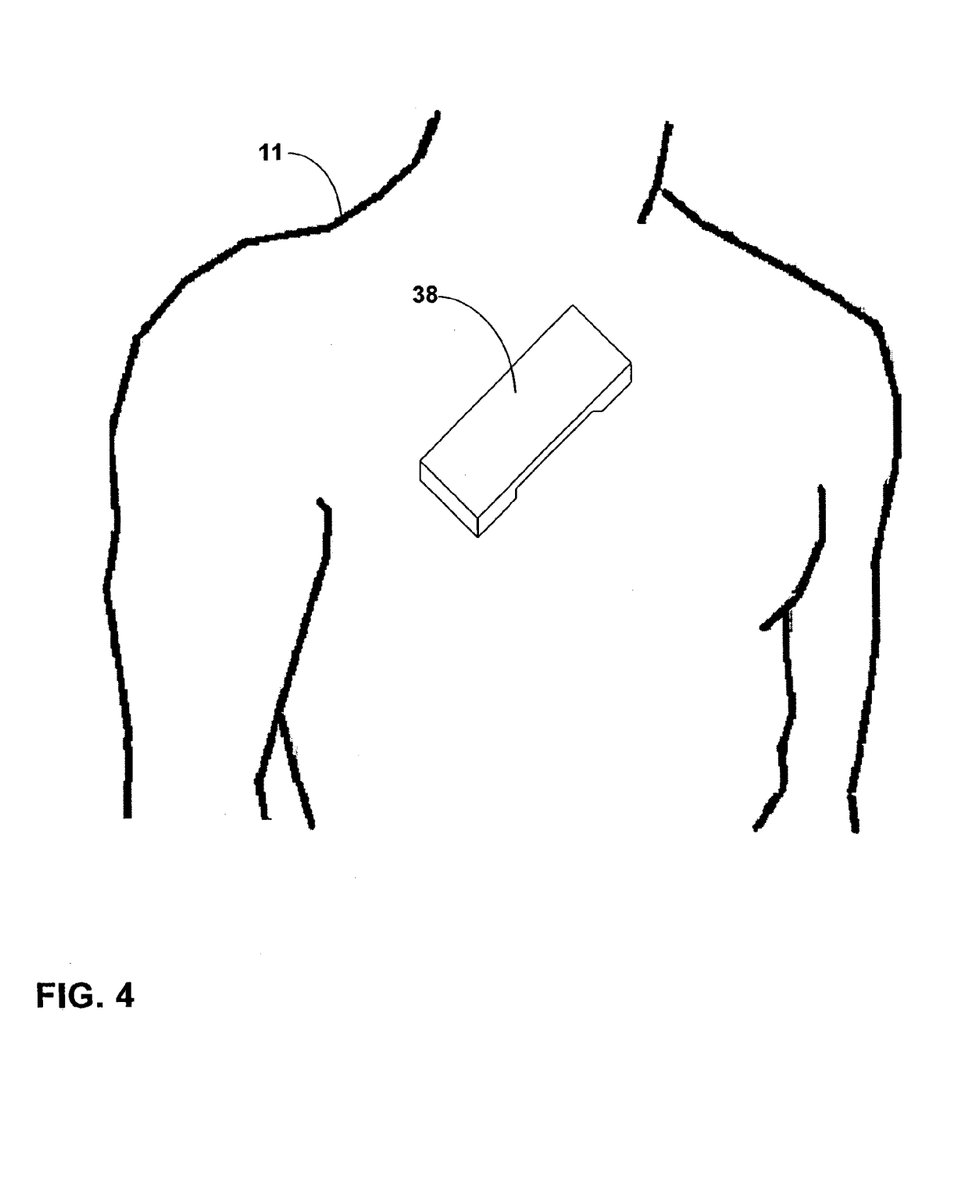
FIG. 4 is a diagram illustrating placement of the telephone handset of FIG. 3 over the chest of a patient.

FIG. 4 is a diagram illustrating placement of the telephone handset 38 of FIG. 3 over the chest of a patient. As shown in FIG. 4, patient 11 places handset 38 against his chest in the proximity of heart 12 and IMD 10 in order to collect surface ECG information from the chest and device information from the IMD. In particular, handset 38 places electrodes 64 and 66 in contact with the chest to obtain the surface ECG information. In addition, handset 38 places RF telemetry wand 62 in proximity with IMD 10, which may be implanted in the upper chest area near one of the patient's clavicles, e.g., in a subpectoral pocket. Thus, as illustrated in FIG. 4, handset 38 simplifies the patient's task in placement of electrodes 64, 66 and RF telemetry wand 62. The patient simply brings handset 38 into contact with the chest near heart 12, and then commences collection of device information and surface ECG information via RF telemetry wand 62 and electrodes 64, 66, respectively.

Figure 5:
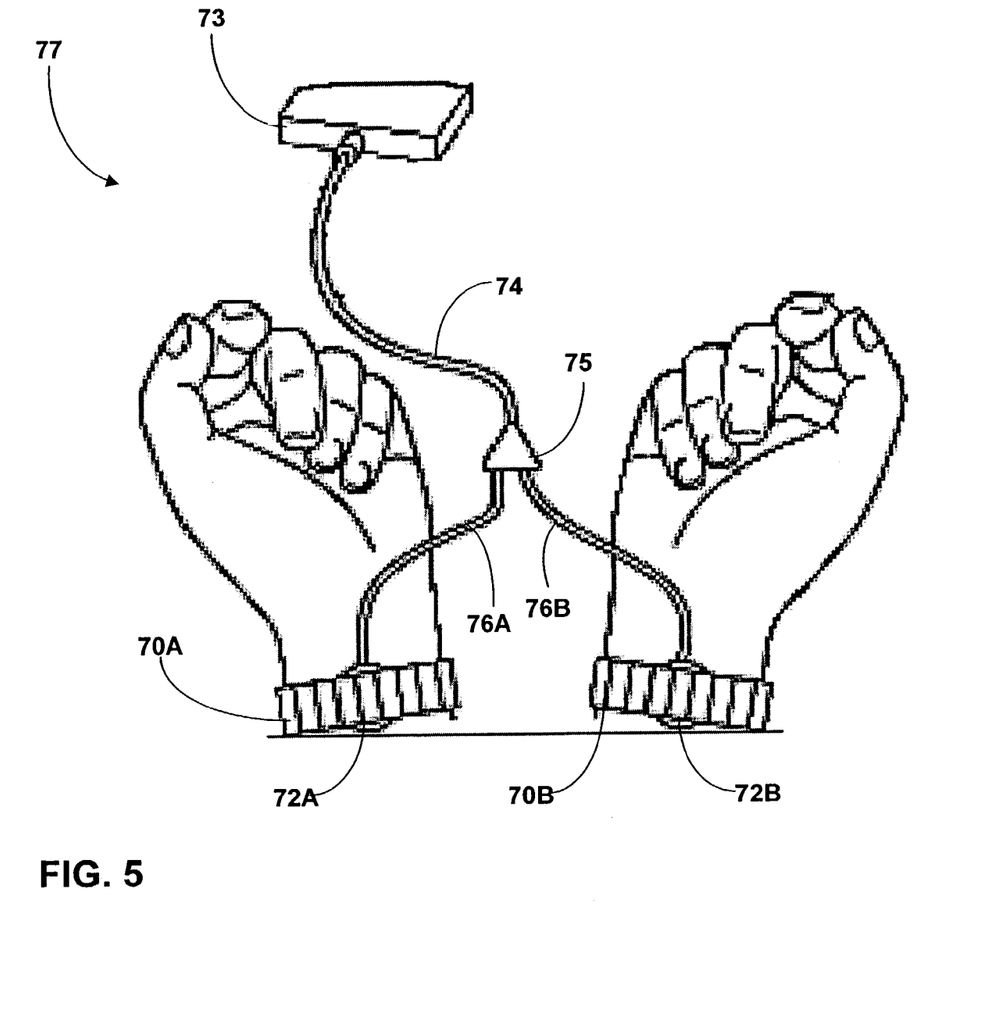
FIG. 5 is a diagram of a wrist electrode arrangement forming part of a device for remote monitoring of implanted medical devices and surface ECG information.

FIG. 5 is a diagram of a wrist electrode arrangement 77 forming part of patient monitoring device 32. As shown in FIG. 5, wrist electrode arrangement 77 includes wrist bands 70A, 70B carrying electrodes 72A, 72B, respectively. A connector plug 73 is designed to mate with port 68 in handset 38 to coupled electrodes 72A, 72B to surface ECG interface circuitry within the handset. Cable 74 carries two conductors that are separated in bifurcator 75 to form two cables 76A, 76B that are electrically coupled to electrodes 72A, 72B. In this manner, wrist electrode arrangement 77 serves as an alternative means for collection of surface ECG information from patient 11. If electrodes 64, 66 are ineffective in obtaining the surface ECG information, for example, the operator of remote monitoring station 30 may instruct patient 11 to instead use wrist electrode arrangement 77.

Figure 6:
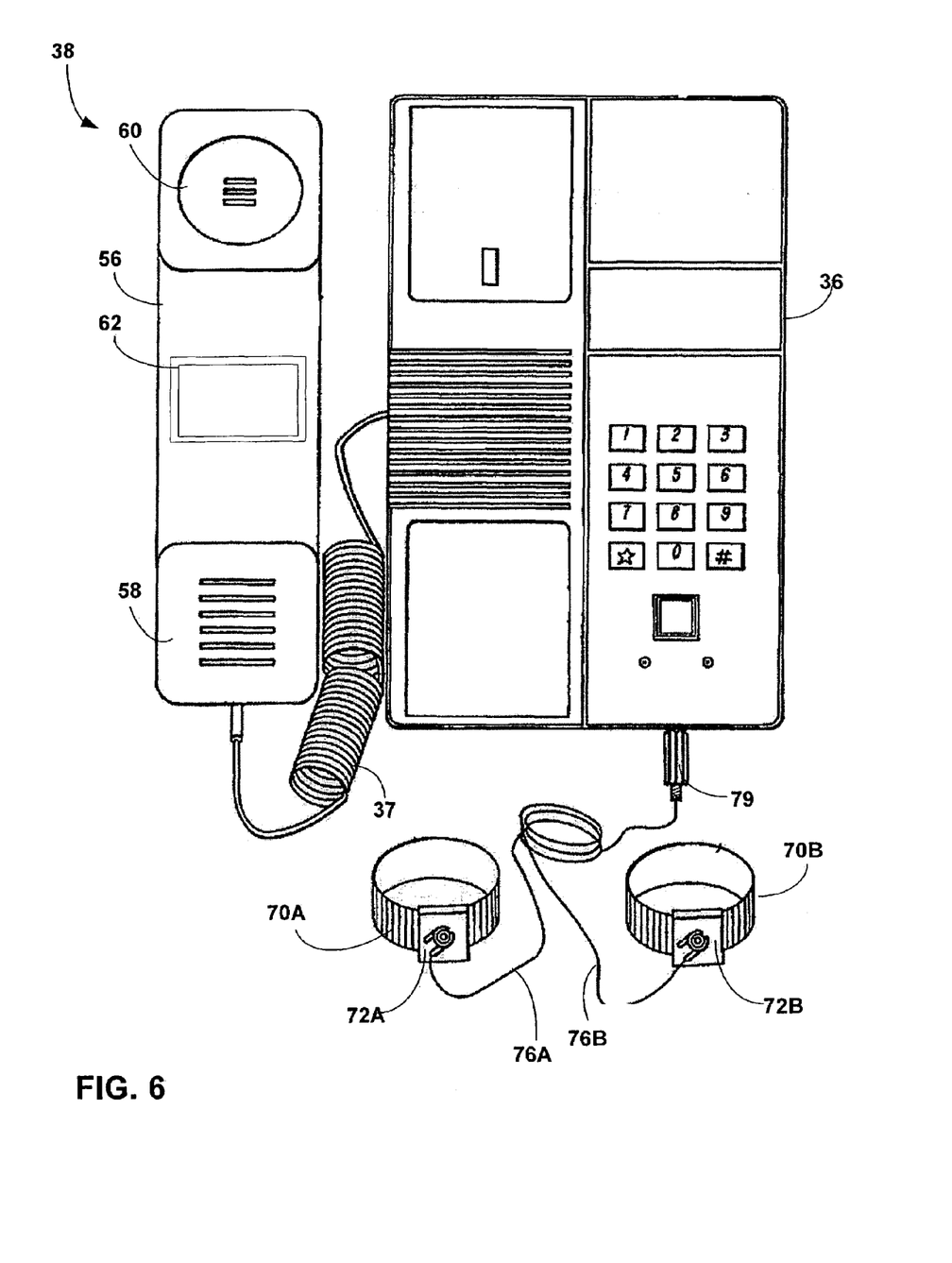
FIG. 6 is a diagram of an alternative telephone handset with another wrist electrode arrangement.

FIG. 6 is a diagram of an alternative telephone handset 38' with another wrist electrode arrangement. As shown in FIG. 6, rather than plugging into handset 38', a pair of wrist bands 70A, 70B with electrodes 72A, 72B may be coupled to telephone base station 36 via wires 76A, 76B and plug 79. In the example of FIG. 6, handset 38' carries RF telemetry wand 40, while telephone base station 36 carries wrist bands 70A, 70B. Accordingly, electronics for collecting device information, such as device parameters and EGM information, may be housed within handset 36, and electronics for collecting surface ECG information may be housed in telephone base station 36.

Figure 7:
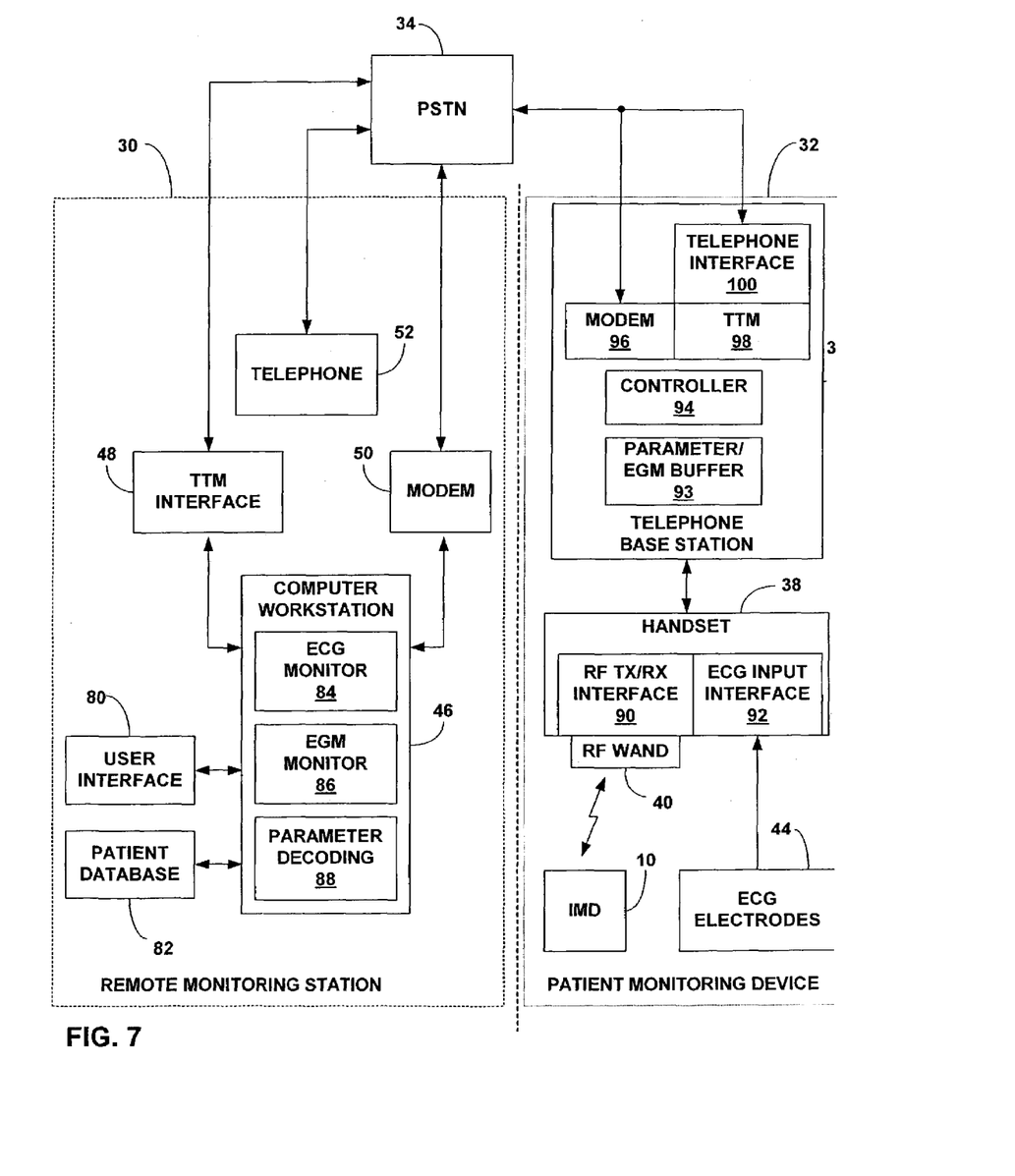
FIG. 7 is a block diagram illustrating the system of FIG. 2 in greater detail.

FIG. 7 is a block diagram illustrating system 28 of FIG. 2 in greater detail. As shown in FIG. 7, computer workstation 46 executes a software application having an ECG monitor module 84, an EGM monitor module 86, and a parameter decoding module 88. ECG monitor module 84 manages processing of surface ECG information received via transtelephonic modulation (TTM) interface 48. In the example of FIG. 7, TTM interface 48 supports transtelephonic frequency modulation. EGM monitor module 86 manages processing of EGM information collected from IMD 10 and received via modem 50. Parameter decoding module 88 manages processing and storage of device parameter information collected from IMD 10 and received via modem 50.

In addition, remote monitoring station 30 includes a user interface 80 to receive user input and present information based on the device information or surface ECG information, e.g., via a display device. Also, remote monitoring station 30 includes a patient database 82 that organizes patient records containing patient test reports. The patient test reports are generated by modules 84, 86, 88 and contain both surface ECG information and device information, such as device parameters of EGM information.

As further shown in FIG. 7, handset 38 includes an RF transmit/receive (TX/RX) interface 90 to drive communication with IMD 10 via RF telemetry wand 40. In addition, handset 38 includes ECG input interface 92 to receive surface ECG information obtained via ECG electrodes 44. ECG input interface 92 includes amplifiers to amply the signals received by ECG electrodes 44. Telephone base station 36 further includes a parameter/EGM buffer 93 to store collected device information prior to transmission of the information to remote monitoring station 30. A controller 94 directs memory transfers for transmission of the device information, and controls a modem 96 to direct the transmission via PSTN 34. In addition, controller 94 directs a transtelephonic modulator (TTM) 98 to control real-time modulation and transmission of surface ECG information to remote monitoring station 30 via telephone interface 100 and PSN 34.

In operation, an operator associated with remote monitoring station 30 places a telephone call to patient 11. Patient 11 is instructed to place ECG electrodes over his chest via handset 36 or on his wrists via wrist bands 70A, 70B. The patient is also required to place wand 40 for telemetry with IMD 10. During this procedure, the operator may communicates with the patient 11 by voice via handset 38 or a speaker phone integrated with telephone base station 36.

The process of communicating with the patient during the implant interrogation would allow obtaining a better quality records while a patient is still on the phone. The improper placement of electrodes and wand could be corrected while the patient is on the phone in the process of monitoring the surface ECG. Additional commands that are sent from the telephone or the keyboard of the remote monitoring station 30 may allow resetting of the modem, instruct the patient via a speaker or provide an alert signal advising the patient to seek medical attention via a patient alert device.

Figure 8:
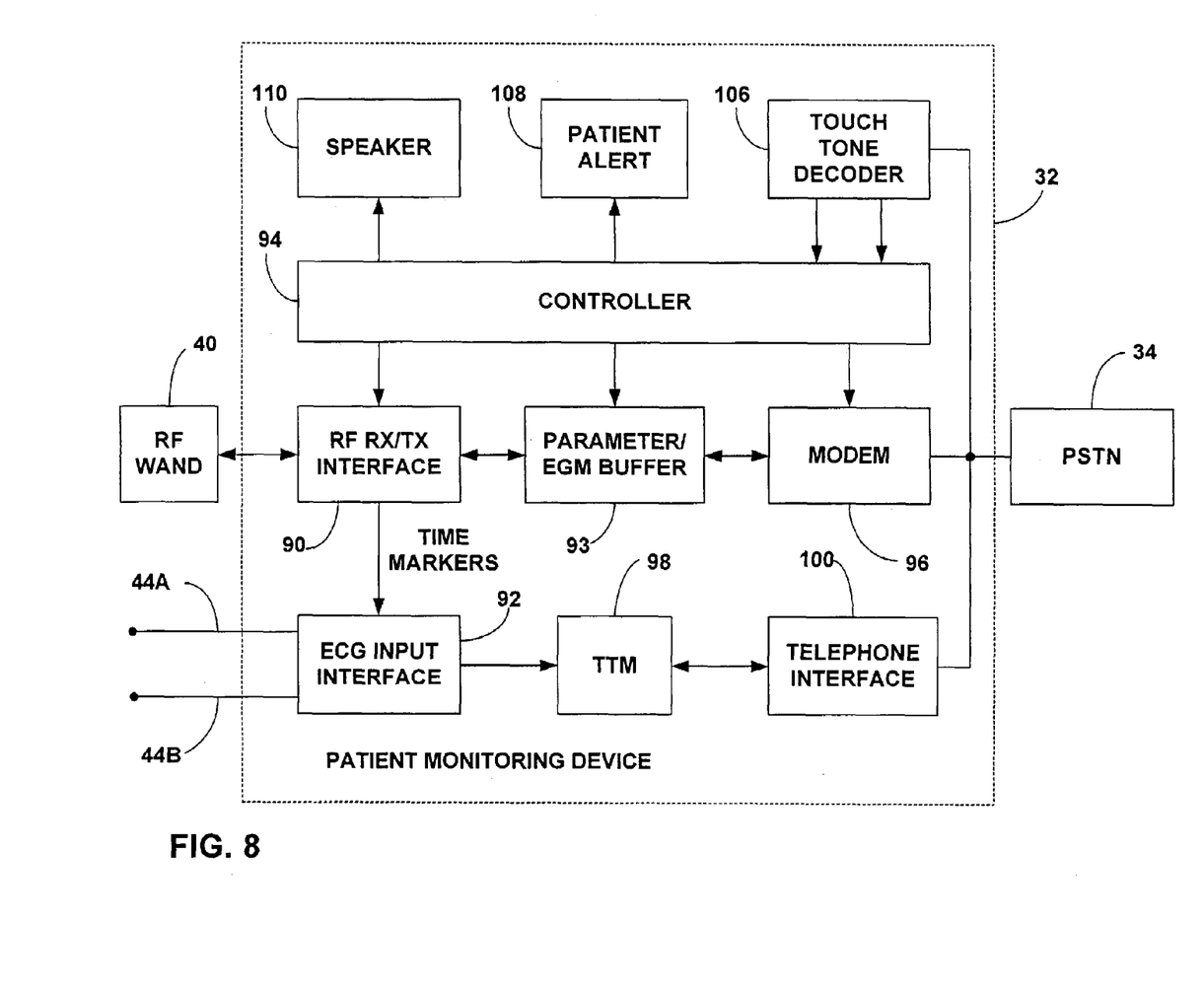
FIG. 8 is a block diagram illustrating an integrated device, for remote monitoring of implanted medical devices and surface ECG information, forming part of the system of FIG. 2.

FIG. 8 is a block diagram illustrating integrated patient monitoring device 32 in greater detail. In the example of FIG. 8, patient monitoring device 32 generally conforms to the device shown in FIG. 7. FIG. 8 further depicts, however, a touch tone decoder 106 that receives a DTMF (dual tone multi frequency) signal when the operator of remote monitoring station 30 presses a key on the touch-tone type telephone 52 (FIG. 2). Each key or sequence of keys corresponds to a command for controller 94. FIG. 8 also shows a patient alert device 108 and a speaker 110.

In operation, RF TX/RX interface 90 receives device parameters and EGM information from IMD 10. Controller 94 controls RF TX/RX interface 90 and parameter/EGM buffer 93 to transfer the information into the parameter/ EGM buffer pending completion of transmission of the surface ECG information. The surface ECG information flows from ECG input interface 92 through TTM 98 and telephone interface 100 and across PSTN 34 to remote monitoring station 30.

RF TX/RX interface 90 also supplies time markers that are superimposed on the ECG signal at the output of ECG input interface 92. Again, the time markers indicate to an operator at remote monitoring station 30 that the device information, i.e., parameters and EGM information, are being collected as transmission of the surface ECG information continues. When a sufficient amount of surface ECG information has been transferred to remote monitoring station 30, controller 94 controls ECG input interface 92 to stop transmission of the surface ECG information. After the transtelephonic transmission of surface ECG information is stopped, controller 94 controls parameter/EGM buffer 93 to transfer its contents to modem 96 for transmission to remote monitoring station 30 via PSTN 34.

The operator at remote monitoring station 30 issues commands to patient monitoring device 32 via transtelephonic transmission. The commands may be received by patient monitoring device 32 while transtelephonic transmission of the surface ECG information is taking place. Touch tone decoder 106 receives a variety of commands from remote monitoring station 30, which enable the remote monitoring station to control collection of information by patient monitoring device 32.

The commands transmitted by remote monitoring station 30 may include: Real Time EGM On/Off, Stored parameters and Stored EGM On/Off, Memory transfer On/Off, TTM transfer On/Off, Speaker On/Off, Patient Alert On/Off, and System Reset. The Real Time ECG On/Off command causes controller 94 to stop or start collection of surface ECG information. The Real Time EGM On/Off command causes controller 94 to start or stop collection of device EGM information from IMD 10.

The Memory transfer On/Off command causes controller 94 to start or stop transfer of device information to and from Parameter/EGM buffer 93. The TTM transfer On/Off command causes controller 94 to stop or start transtelephonic transmission. The Speaker On/Off command causes controller 94 to turn speaker 110 on or off. The Patient Alert On/Off command causes controller 94 to turn speaker 108 on or off. The System Reset command causes controller 94 to reset patient monitoring device 32.

In operation, the operator of remote monitoring station 30 speaks on the telephone with patient 11, and instructs the patient to place handset 38 proximate the implant area on the patient's chest. As soon as the patient palaces electrodes properly on the chest, the surface ECG can be transferred to remote monitoring station 30. The operator observes the surface ECG information, which may be a waveform, on a display device. The surface ECG waveform may include regular spikes every few seconds, which represent the time markers generated by RF TX/RX interface 90.

The time markers indicate that RF telemetry wand 40 is properly placed relative to IMD 10 and that RF transmission is taking place. A touch tone command sent by the operator will start collection of device parameters and EGM information. When the operator determines that a sufficient, artifact free sample of the surface ECG is collected in the presence of the EGM, the operator sends another command to transfer the stored implant parameters and stored EGM records from patient monitoring device 32 to remote monitoring station 30 via PSTN 34.

Figure 9:
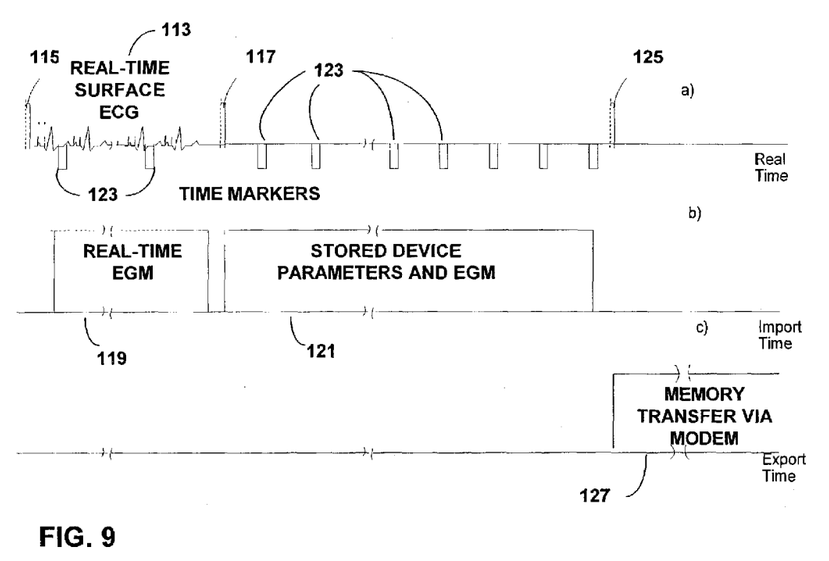
FIG. 9 is a block diagram illustrating operation of a remote monitoring station forming part of the system of FIG. 2.

FIG. 9 is a chart illustrating collection of device information and surface ECG information. As shown in FIG. 9, patient monitoring device 32 transmits a real-time surface ECG information in the form of an ECG waveform 113. ECG waveform 113 is preceded by a synchronization marker 115 and followed by a synchronization marker 117. While the real-time surface ECG information is being transmitted, patient monitoring device 32 also obtains real-time EGM information from IMD 10 via RF telemetry, as indicated by reference numeral 119.

Then, patient monitoring device 32 obtains stored parameters and stored EGM information from IMD 10, as indicated by reference numeral 121. Transmission of the surface ECG information from patient monitoring device 32 to remote monitoring device 30 can be referred to as real-time. Transmission of real-time and stored device information from IMD 10 to patient monitoring device 32 can be referred to as import time. Transmission of the real-time and stored device information from patient monitoring device 32 to remote monitoring device 30 can be referred to as export time.

Patient monitoring device 32 generates time markers 123 and superimposes the time markers on the TTM channel transmitted to remote monitoring station 30. The time markers 123 on the TTM channel indicate that the telemetry process is taking place between patient monitoring device 32 and IMD 10. Once the time markers stop appearing on the transtelephonic transmission of ECG information, the operator at remote monitoring station 30 determines that the telemetry is over, and that the device information has been successfully transferred to patient monitoring device 32.

A synchronization marker 125 is placed at the end of the time markers 123. The operator then contacts patient 11, terminates the voice transmission, and starts transmission of digital data via modem 96 to transfer the device information, as indicated by reference number 127 The device information may include the real time EGM 119 and stored device parameters and stored EGM information 121 accumulated during the telemetry process.

Remote monitoring station 30 transmits the real-time EGM On command to activate the telemetry between IMD 10 and patient monitoring device 32 for real-time EGM transmission. At the same time, the real-time EGM On command indicates to RF TX/RX interface 90 that, at the start of the real time telemetry of the EGM data, the synchronization marker signal must be sent to ECG input interface 92 to indicate the starting time of EGM recording. This first synchronization marker will allow synchronizing the real time surface ECG recording with the EGM recording transmitted by RF TX/RX interface 90. The final synchronization can be done by remote monitoring station 30.

The purpose for such synchronization is to be able to display surface ECG and device EGM in the same time domain for clinical evaluation.

When the operator is satisfied that an acceptable sample of surface ECG has been obtained, along with a steady stream of time marker pulses, the operator issues a Stored parameters and Stored EGM On command. This command stops the real time EGM telemetry. This command also indicate to RF TX/RX interface 90 to send another synchronization pulse that will indicate the start of transfer of stored device parameters and stored EGM information. A stream of Time Markers will continue appearing on the TTM channel during importation of the stored parameters and stored EGM information from IMD 10 to patient monitoring device 32. These time markers will appear on the TTM channel for as long as the parameters and stored EGM information take to transfer. When the transfer of parameters and stored EGM information stops, the time markers stop appearing on the TTM channel. At this point, remote monitoring station 30 issues the Memory transfer On/Off command to cause patient monitoring device 32 to transmit the real time EGM, stored parameters and stored EGM information.

Figure 10:
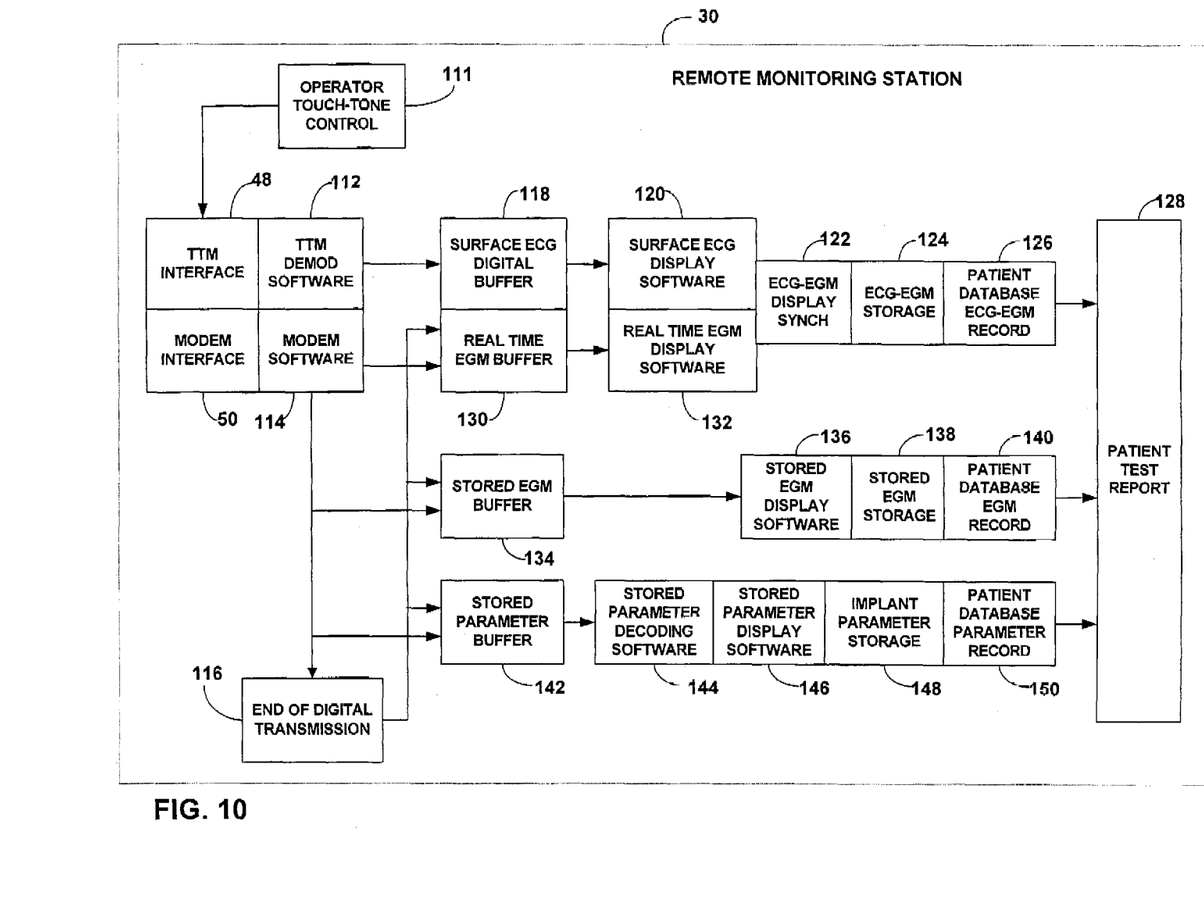
FIG. 10 is a chart illustrating collection of implanted medical device information and surface ECG information.

FIG. 10 is a block diagram illustrating operation of a remote monitoring station 30 in greater detail. As shown in FIG. 10, remote monitoring station 30 receives touch-tone control input 111 for communication to patient monitoring device 32 via TTM interface 48. The signals into transtelephonic interface 48 and modem interface 50 are received from PSTN 34. Transtelephonic demodulation software 112 converts the signal into digital format and places it in surface ECG digital buffer 118 while the modem software 114 fills real time EGM buffer 130, stored EGM buffer 134 and stored parameter buffer 142. Modem software 114 identifies real time EGM information, stored EGM information, and stored device parameters, as discussed above with reference to the diagram of FIG. 9, and the information encoded into the structure of digital data obtained from modem interface 50.

Surface ECG display software 120 and real-time EGM display software 132 are adjusted in accordance with the synchronization markers transmitted on the TTM channel by ECG-EGM display synchronization software 122. Stored parameter decoding software 144 decodes parameter information to a form suitable of presentation by stored parameter display software 146. The second synchronization marker represents the end of the real time EGM recording. The time markers on TTM transmissions will indicate that telemetry between IMD 10 and patient monitoring device 32 is taking place.

When the operator realizes that there are no further time markers, the operator sends a command to start transfer of the contents of the parameter/EGM buffer 93. Upon the end of the transmission, a modem interface software end of digital transmission signal 116 is sent to buffers 130, 134, 142 to initiate software 120, 132, 144, 146 for displaying surface ECG, real time EGM and stored parameters. The synchronization maker permits the operator to verify and, if necessary, adjust the relative position of the surface ECG and the real time EGM on a display device. The operator will have the opportunity to review the stored EGM as well as stored device parameters in conjunction with the real-time EGM and surface ECG information. Remote monitoring station 30 then stores the pertinent information, e.g., via ECG-EGM storage software 124, stored EGM storage software 138, and parameter storage software 148. The stored information can be stored in a database in a patient record 128, as prepared by patient database ECG-EGM record software 126, patient database EGM record software 140, patient database parameter software 150. Upon storing the result of test the system operator can generate reports that summarize patient test results.

Figure 11:
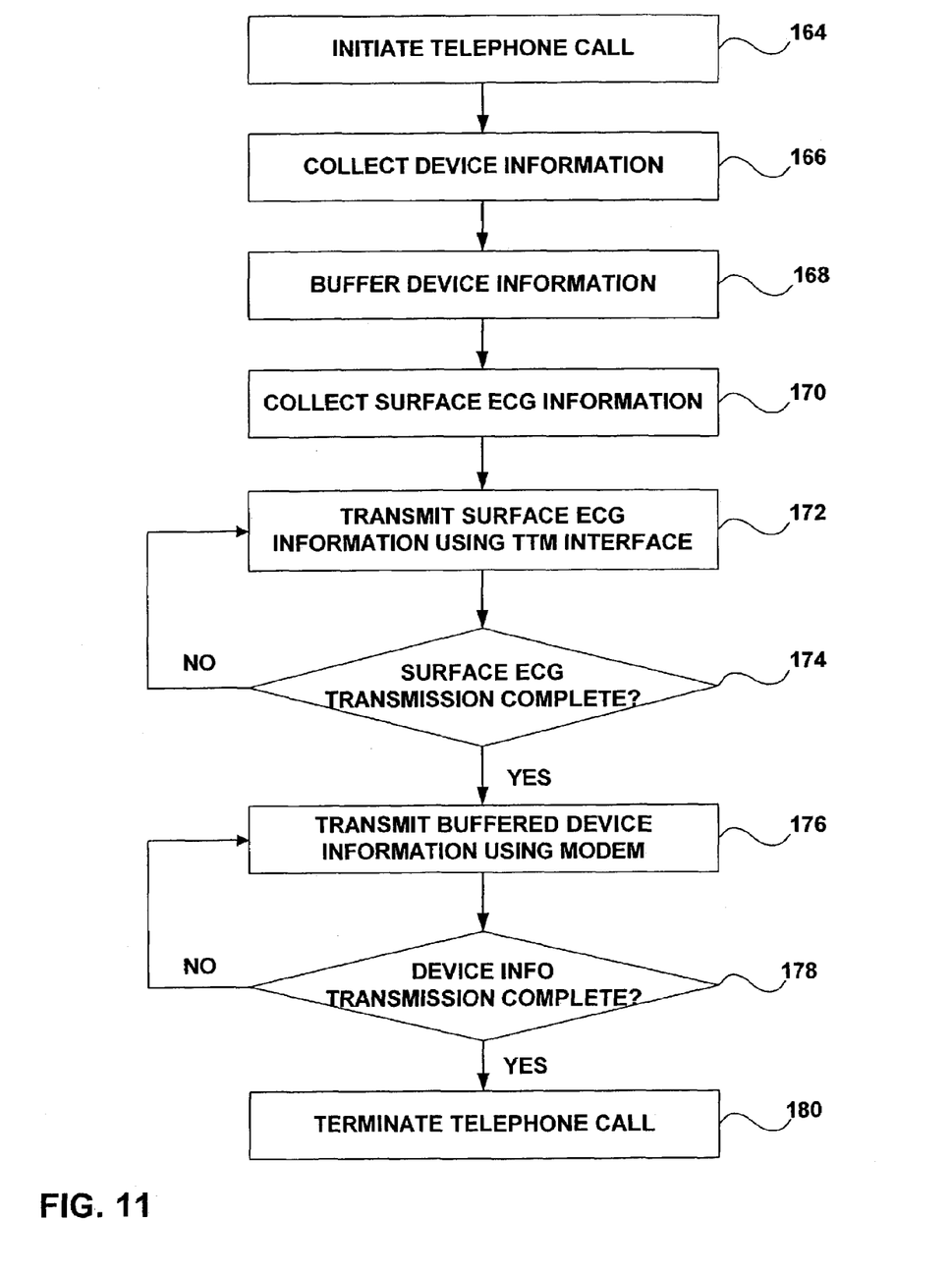
FIG. 11 is a flow diagram illustrating a process for remote monitoring of implanted medical devices and surface ECG information.

FIG. 11 is a flow diagram illustrating a process for remote monitoring of implanted medical devices and surface ECG information. As shown in FIG. 11, the process involves initiating a telephone call (164), collecting device information (166) from IMD 10 and buffering the device information (168). The process also involves collecting surface ECG information (170), and transmitting the surface ECG information from patient monitoring device 32 to remote monitoring station 30 using a TTM interface (172). When the surface ECG transmission is complete (174), the process further involves transmitting the buffered device information from patient monitoring device 32 to remote monitoring station 30 using a modem (176). Once the transmission of device information is complete (178), the telephone call is terminated (180).

Figure 12:
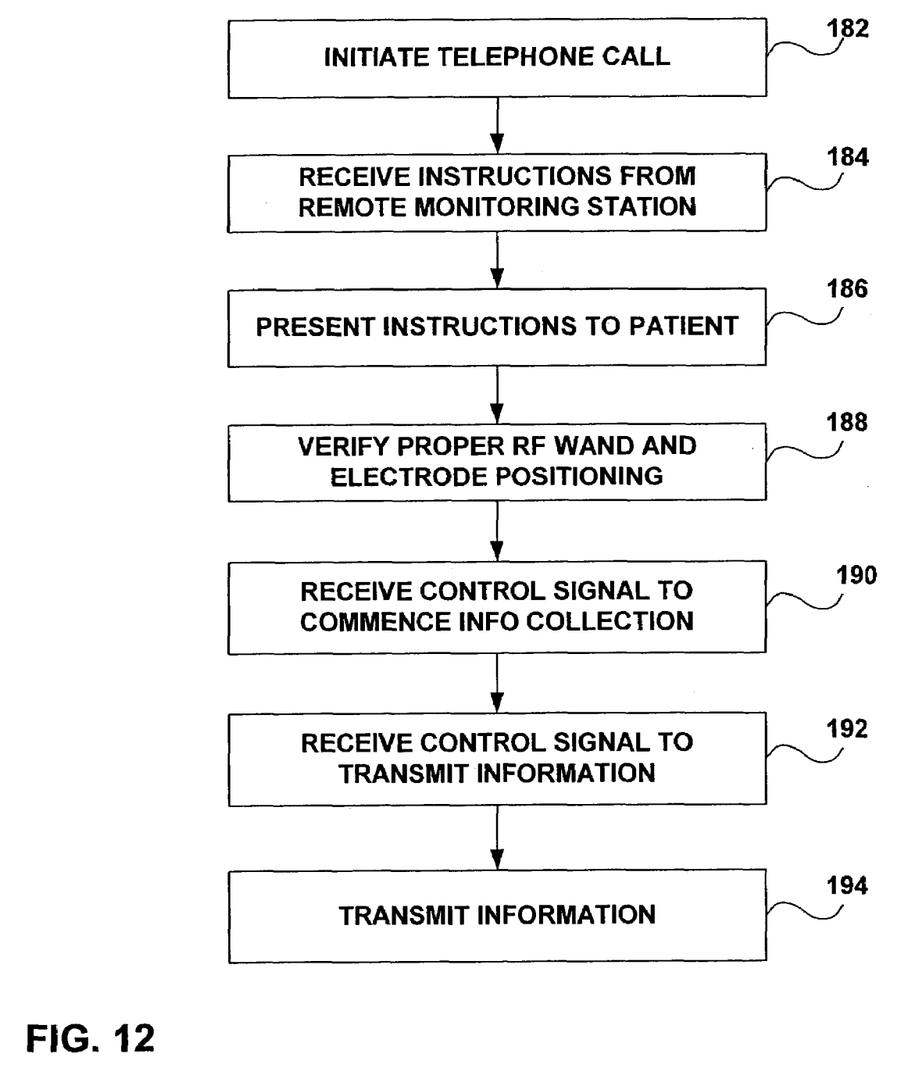
FIG. 12 is a flow diagram illustrating additional details of the process of FIG. 10.

FIG. 12 is a flow diagram illustrating additional details of the process of FIG. 9. As shown in FIG. 12, upon initiation of a telephone call (182), instructions are received from remote monitoring station 30 (184). Patient monitoring device 32 presents the instructions to patient 11 (186), e.g., visually or audibly. The instructions may include instructions for proper positioning of electrodes, an RF telemetry wand, or both. Upon verification of proper RF wand and electrode positioning (188), patient monitoring device 32 receives a control signal from remote monitoring station 30 to commence collection of information (190). Then, remote monitoring station 30 receives a control signal to transmit the collected information (192), and responds by transmitting the information (194). The transmission of the information may be in an order and format as described above with reference to the diagram of FIG. 9.

Some of the techniques described herein may be embodied as a computer-readable medium comprising instructions for a programmable processor. The programmable processor may include one or more individual processors, which may act independently or in concert. A "computer-readable medium" includes but is not limited to read-only memory, Flash memory and a magnetic or optical storage medium.

Various embodiments of the invention have been described. However, one skilled in the art will appreciate that various modifications may be made to these embodiments without departing from the scope of the invention. These and other embodiments are within the scope of the following claims. These and other embodiments are within the scope of the following claims.

What is claimed is:

1. A patient monitoring device comprising:
   a telemetry interface to collect device information from an implanted medical device within a patient;
   a surface electrocardiogram (ECG) interface to collect surface ECG information from the patient simultaneously with collection of the device information and to provide synchronization markers with the collected surface ECG information that identify a time period when the ECG information and the device information are being collected simultaneously, to allow synchronization of the device information with the surface ECG information; and
   a telecommunication interface to transmit sequentially the surface ECG information and the device information to a remote monitoring station.

2. The device of claim 1, wherein the telemetry interface includes a radio frequency wand for placement in proximity with the implanted medical device.

3. The device of claim 1, wherein the surface ECG interface includes electrodes for placement on the patient.

4. The device of claim 3, further comprising wristbands that carry the electrodes.

5. The device of claim 3, further comprising a telephone handset that includes the surface ECG interface and the electrodes, wherein the telephone handset communicates with the telecommunication interface.

6. The device of claim 5, wherein the telephone handset comprises a mobile telephone handset.

7. The device of claim 3, wherein the telemetry interface includes a radio frequency wand for placement in proximity with the implanted medical device, the device further comprising a telephone handset that integrates the wand, the surface ECG interface and the electrodes.

8. The device of claim 7, wherein the wand and the electrodes are positioned on the handset to facilitate placement of the wand relative to the implanted medical device and placement of the electrodes in positions suitable for surface ECG monitoring when the handset is placed in contact with an upper chest region of the patient.

9. The device of claim 1, wherein the telemetry interface includes a radio frequency wand for placement in proximity with the implanted medical device, the device further comprising a telephone handset that integrates the wand.

10. The device of claim 9, wherein the telephone handset includes the surface ECG interface and a connection terminal to receive surface ECG electrodes.

11. The device of claim 10, wherein the ECG electrodes include adhesive-backed electrodes for placement on the patient.

12. The device of claim 10, further comprising wristbands that carry the ECG electrodes.

13. The device of claim 1, further comprising:
a memory to store the device information collected from the implanted medical device; and
a controller to selectively transmit the surface ECG information and the stored device information to the remote monitoring station via the telecommunication interface.

14. The device of claim 13, wherein the controller drives simultaneous collection of the device information and the surface ECG information.

15. The device of claim 14, further comprising:
a modem to transmit the device information to the remote monitoring station; and
a transtelephonic frequency modulator to transmit the surface ECG information.

16. The device of claim 13, wherein the controller generates time markers in response to collection of the device information, and incorporates the time markers in the surface ECG information.

17. The device of claim 13, wherein the controller is responsive to a control signal received from the remote monitoring station via the telecommunication interface to drive collection and transmission of the device information and the surface ECG information.

18. The device of claim 1, wherein the device information includes device parameter information and internal electrogram information obtained by the implanted medical device.

19. The device of claim 1, wherein the telecommunication interface includes a public switched telephone network interface.

20. The device of claim 1, wherein the telecommunication interface transmits the device information and the surface ECG information to the remote monitoring station within a single telephone call established by the telecommunication interface.

21. The device of claim 1, further comprising an output device to present information communicated to the device by the remote monitoring station.

22. A method comprising:
collecting device information from an implanted medical device within a patient;
collecting surface electrocardiogram (ECG) information from the patient simultaneously with the collecting of the device information;
providing synchronization markers with the collected surface ECG information that identify a time period when the ECG information and the device information are being collected simultaneously to allow synchronization of the device information with the surface ECG information; and
transmitting sequentially the surface ECG information and the device information to a remote monitoring station via a common telephone interface.

23. The method of claim 22, further comprising transmitting the device information and the surface ECG information to the remote monitoring station in the course of a single telephone call.

24. The method of claim 22, further comprising collecting the device information from the implanted medical device via a radio frequency wand placed in proximity with the implanted medical device.

25. The method of claim 22, further comprising collecting the surface ECG information via surface ECG electrodes placed on the patient.

26. The method of claim 25, further comprising collecting the surface ECG information from wristbands that carry the electrodes.

27. The method of claim 25, further comprising collecting the surface ECG information from a telephone handset that includes the surface ECG electrodes, wherein the handset is placed on the patient to cause contact between the surface ECG electrodes and the patient, and wherein the telephone handset communicates with the telephone interface.

28. The method of claim 27, wherein the telephone handset comprises a mobile telephone handset.

29. The method of claim 27, further comprising collecting the device information from the implanted medical device via a radio frequency wand placed in proximity with the implanted medical device, wherein the telephone handset integrates the wand and the electrodes.

30. The method of claim 29, wherein the wand and the electrodes are positioned on the handset to facilitate placement of the wand relative to the implanted medical device and placement of the electrodes in positions suitable for surface ECG monitoring when the handset is placed in contact with an upper chest region of the patient.

31. The method of claim 30, wherein the telephone handset includes the surface ECG interface and a connection terminal to receive surface ECG electrodes.

32. The method of claim 31, wherein the ECG electrodes include adhesive-backed electrodes for placement on the patient, the method further comprising adhering the electrodes to the patient.

33. The method of claim 31, further comprising attaching wristbands that carry the ECG electrodes to the patient.

34. The method of claim 22, further comprising:
storing the device information collected from the implanted medical device in a memory; and selectively transmitting the surface ECG information and the stored device information to the remote monitoring station.

35. The method of claim 34, further comprising simultaneously collecting the device information and the surface ECG information.

36. The method of claim 35, further comprising:
transmitting the device information to the remote monitoring station via a modem; and
transmitting the surface ECG information via a transtelephonic modulator.

37. The method of claim 34, further comprising generating time markers in response to collection of the device information, and incorporating the time markers in the surface ECG information.

38. The method of claim 34, further comprising receiving a control signal received from the remote monitoring station, and collecting and transmitting the device information and the surface ECG information in response to the control signal.

39. The method of claim 22, wherein the device information includes device parameter information and internal electrogram information obtained by the implanted medical device.

40. The method of claim 22, further comprising transmitting the device information and the surface ECG information via a public switched telephone network interface.

41. The method of claim 22, further comprising transmitting the device information and the surface ECG information to the remote monitoring station within a single telephone call.

42. The method of claim 22, further comprising presenting to the patient information communicated to the device by the remote monitoring station.

43. A patient monitoring system comprising:
a remote monitoring station; and
a patient monitoring device including a telemetry interface to collect device information from an implanted medical device within a patient, a surface electrocardiogram (ECG) interface to collect surface ECG information from the patient simultaneously with the collection of the device information and provide synchronization markers with the collected surface ECG information that identify a time period when the ECG information and the device information are being collected simultaneously to allow synchronization of the device information with the surface ECG information, a telecommunication interface to transmit sequentially the surface ECG information and the device information to the remote monitoring station.

44. The system of claim 43, wherein the remote monitoring station includes a transtelephonic interface to receive the surface ECG information, and a modem interface to receive the device information.

45. The system of claim 43, wherein the remote monitoring station includes a report generation module to present the surface ECG information and the device information.

46. The system of claim 43, wherein the patient monitoring device includes a telemetry interface having a radio frequency wand for placement in proximity with the implanted medical device.

47. The system of claim 43, wherein the patient monitoring device includes a surface ECG interface having electrodes for placement on the patient.

48. The system of claim 47, further comprising a telephone handset that includes the surface ECG interface and the electrodes, wherein the telephone handset communicates with the telecommunication interface.

49. The system of claim 48, wherein the telephone handset comprises a mobile telephone handset.

50. The system of claim 47, wherein the telemetry interface includes a radio frequency wand for placement in proximity with the implanted medical device, the device further comprising a telephone handset that integrates the wand, the surface ECG interface and the electrodes.

51. The system of claim 43, wherein the patient monitoring device includes:
a memory to store the device information collected from the implanted medical device; and
a controller to selectively transmit the surface ECG information and the stored device information to the remote monitoring station via the telecommunication interface.

52. The system of claim 51, wherein the controller drives simultaneous collection of the device information and the surface ECG information.

53. The system of claim 52, wherein the patient monitoring device includes a modem to transmit the device information to the remote monitoring station, and a transtelephonic modulator to transmit the surface ECG information.

54. The system of claim 51, wherein the controller generates time markers in response to collection of the device information, and incorporates the time markers in the surface ECG information.

55. The system of claim 51, wherein the controller is responsive to a control signal received from the remote monitoring station via the telecommunication interface to drive collection and transmission of the device information and the surface ECG information.

56. The system of claim 43, wherein the device information includes device parameter information and internal electrogram information obtained by the implanted medical device.

57. The system of claim 43, wherein the telecommunication interface includes a public switched telephone network interface.

58. The system of claim 43, wherein the telecommunication interface transmits the device information and the surface ECG information to the remote monitoring station within a single telephone call established by the telecommunication interface.

59. The system of claim 43, further comprising an output device to present information communicated to the device by the remote monitoring station.

* * * * *